Figure 1:
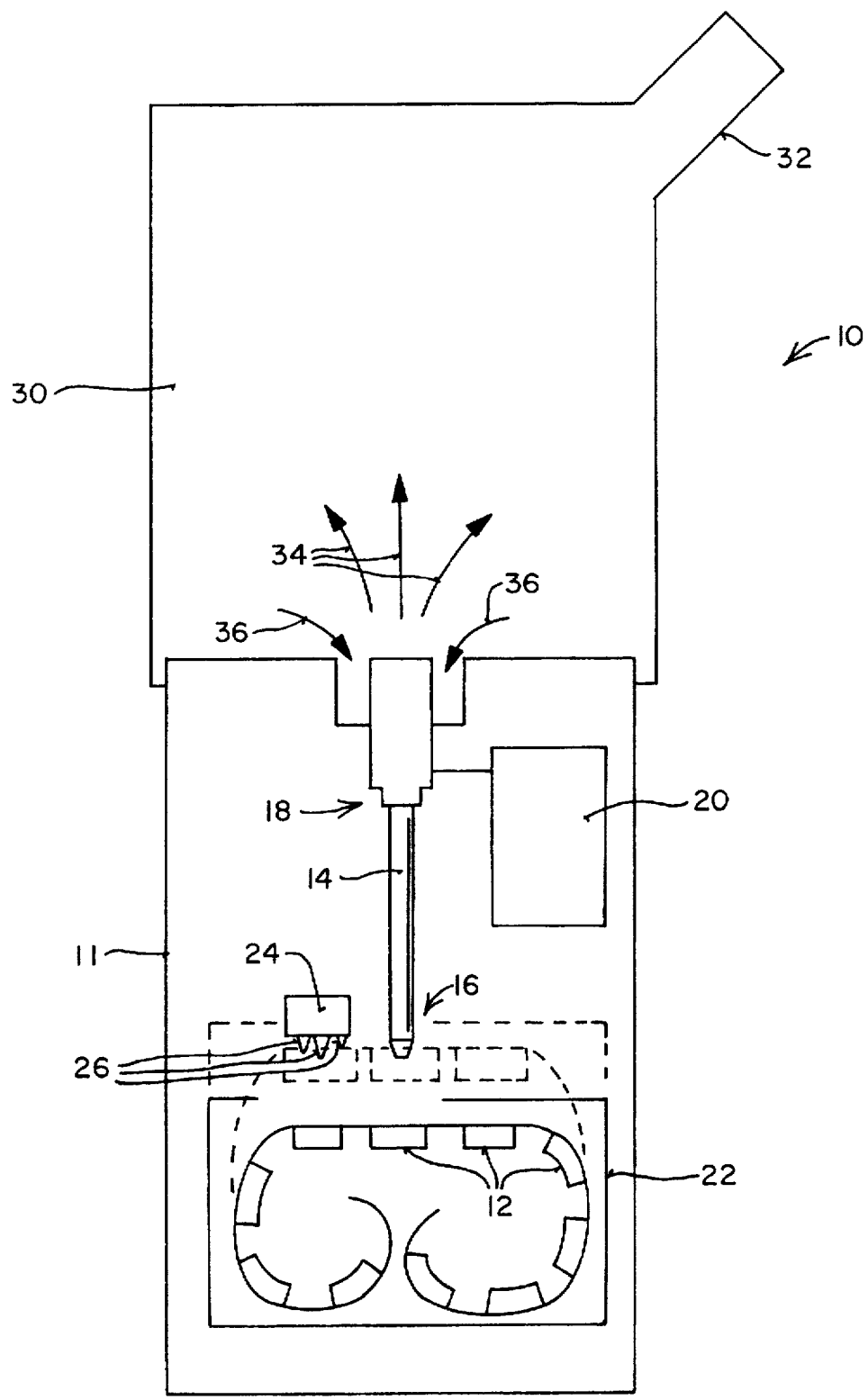

US005785049A

United States Patent [19]
Smith et al.

[11] Patent Number: 5,785,049
[45] Date of Patent: Jul. 28, 1998

[54] METHOD AND APPARATUS FOR DISPERSION OF DRY POWDER MEDICAMENTS

[75] Inventors: Adrian E. Smith, Belmont; John D. Burr, Redwood City; Jeffery W. Etter, Castro Valley; George S. Axford, Menlo Park; Shirley W. Lyons, Redwood City; Robert M. Platz, Half Moon Bay, all of Calif.

[73] Assignee: Inhale Therapeutic Systems, Palo Alto, Calif.

[21] Appl. No.: 309,691

[22] Filed: Sep. 21, 1994

[51] Int. Cl.$^6$ .................. A61M 15/00; A61M 16/00; B05D 7/14; B65D 83/06
[52] U.S. Cl. .................. 128/203.15; 128/203.21; 206/528
[58] Field of Search .................. 128/203.15, 203.21, 128/203.23; 604/58; 206/528

[56] References Cited

U.S. PATENT DOCUMENTS

| 478,744 | 7/1892 | Evans | 128/203.15 |
| 513,189 | 1/1894 | Knode | 128/203.15 |

(List continued on next page.)

FOREIGN PATENT DOCUMENTS

| 0347779 | 12/1989 | European Pat. Off. . |
| 0467172 | 1/1992 | European Pat. Off. . |
| 0468914 | 1/1992 | European Pat. Off. . |
| 0490797 | 6/1992 | European Pat. Off. . |
| 7712041 | 5/1979 | Netherlands . |
| 0628930 | 9/1978 | U.S.S.R. . |
| 1003926 | 3/1983 | U.S.S.R. . |
| 9007351 | 7/1990 | WIPO . |
| 9102558 | 3/1991 | WIPO . |
| 9309832 | 5/1993 | WIPO . |
| 9408552 | 4/1994 | WIPO . |

OTHER PUBLICATIONS

Fox and Westaway (1988) "Perform. of venturi educator as feeder in pneumatic conveying system." *Powder and Bulk Engin.* Mar. 1988.
Pittman (1986) Solids Handling Conference. Paper C4 pp. C–41 to C–51.
Witham and Gates "Dry Dispersion With Sonic Velocity Nozzles" Wrkshp on Dissemination Techniques, Chemical Systems Lab, MD.
Zholob and Koval (1978) "Effect of Injector Unit on Particle Size of Atomized Powder" *Poroshkovaya Metallurgiya*, No. 6/198 pp. 13–16.
Bohnet (1984) "Calculation and Design of Gas/Solid–Injectors" *Powder Technology*, pp. 302–313.
Budrik and Zhelonkina (1978) "Ejector Feeders for Pneumatic Transport Systems," *Chemical and Petroleum Engineering* vol. 14.
Chemical Engineers' Handbook, Fifth Edition, prepared under editorial direction of Robert H. Perry, Ejectors, pp. 6–29 through 5–32.

*Primary Examiner*—Kimberly L. Asher
*Attorney, Agent, or Firm*—Townsend and Townsend and Crew LLP

[57] ABSTRACT

A method for aerosolizing a powdered medicament comprises coupling a powder inlet end of a feed tube with a penetration in a receptacle containing the powder. Powder is drawn upward through the tube and dispersed in a high pressure gas stream flowing past a portion of the feed tube. Apparatus comprise the feed tube mounted within a base enclosure proximate a holder for one or more receptacles, which may be in the form of a cartridge containing a plurality of receptacles formed in a continuous web. The cartridge may be reciprocated relative to the feed tube and a separate piercing mechanism in order to sequentially piercing the receptacle and thereafter couple the feed tube through the resulting penetration for extracting the powder. Alternatively, penetration(s) through the receptacle may be formed as the feed tube is coupled, or some penetrations formed prior to coupling with other penetrations formed at the time of coupling.

50 Claims, 10 Drawing Sheets

U.S. PATENT DOCUMENTS

| | | | |
|---|---|---|---|
| 2,533,065 | 12/1950 | Taplin et al. | 128/203.15 |
| 2,549,303 | 4/1951 | Friden | 128/203.21 |
| 2,570,774 | 10/1951 | Davis | 128/203.15 |
| 2,603,216 | 7/1952 | Taplin et al. | 128/203.15 |
| 3,425,600 | 2/1969 | Abplanalp . | |
| 3,921,637 | 11/1975 | Bennie et al. . | |
| 3,967,761 | 7/1976 | Melton, Jr. et al. | 128/203.21 |
| 3,991,761 | 11/1976 | Cocozza . | |
| 3,994,421 | 11/1976 | Hansen . | |
| 4,069,819 | 1/1978 | Valentini et al. . | |
| 4,105,027 | 8/1978 | Lundquist . | |
| 4,114,615 | 9/1978 | Wetterlin . | |
| 4,249,526 | 2/1981 | Dean et al. . | |
| 4,338,931 | 7/1982 | Cavazza . | |
| 4,446,862 | 5/1984 | Baum et al. . | |
| 4,627,432 | 12/1986 | Newell et al. . | |
| 4,807,814 | 2/1989 | Douche et al. . | |
| 4,811,731 | 3/1989 | Newell et al. . | |
| 4,884,565 | 12/1989 | Cocozza . | |
| 4,889,114 | 12/1989 | Kladders . | |
| 4,995,385 | 2/1991 | Valentini et al. . | |
| 5,035,237 | 7/1991 | Ramella . | |
| 5,048,514 | 9/1991 | Ramella . | |
| 5,186,166 | 2/1993 | Riggs et al. | 128/203.15 |
| 5,207,217 | 5/1993 | Cocozza et al. | 128/203.15 |
| 5,287,850 | 2/1994 | Haber et al. | 128/203.21 |
| 5,337,740 | 8/1994 | Armstrong et al. | 128/203.12 |
| 5,355,872 | 10/1994 | Riggs et al. | 128/200.21 |
| 5,533,502 | 7/1996 | Piper | 128/203.15 |

METHOD AND APPARATUS FOR DISPERSION OF DRY POWDER MEDICAMENTS

BACKGROUND OF THE INVENTION

1. Field of the Invention

The present invention relates generally to methods and apparatus for the pulmonary delivery of drugs. More particularly, the present invention relates to a method and apparatus for dispersing dry powder medicaments for inhalation by a patient.

Effective delivery to a patient is a critical aspect of any successful drug therapy. Various routes of delivery exist, and each has its own advantages and disadvantages. Oral drug delivery of pills, capsules, elixirs, and the like, is perhaps the most convenient method, but many drugs are degraded in the digestive tract before they can be absorbed. Such degradation is a particular problem with modern protein drugs which are rapidly degraded by proteolytic enzymes in the digestive tract. Subcutaneous injection is frequently an effective route for systemic drug delivery, including the delivery of proteins, but enjoys a low patient acceptance. Since injection of drugs, such as insulin, one or more times a day can frequently be a source of poor patient compliance, a variety of alternative routes of administration have also been developed, including transdermal, intranasal, intrarectal, intravaginal, and pulmonary delivery.

Of particular interest to the present invention, pulmonary drug delivery relies on inhalation of a drug dispersion or aerosol by the patient so that active drug within the dispersion can reach the distal (alveolar) regions of the lung. It has been found that certain drugs are readily absorbed through the alveolar region directly into blood circulation. Pulmonary delivery is particularly promising for the delivery of proteins and polypeptides which are difficult to deliver by other routes of administration. Such pulmonary delivery is effective both for systemic delivery and for localized delivery to treat diseases of the lungs.

Pulmonary drug delivery (including both systemic and local) can itself be achieved by different approaches, including liquid nebulizers, metered dose inhalers (MDI's) and dry powder dispersion devices. Dry powder dispersion devices are particularly promising for delivering protein and polypeptide drugs which may be readily formulated as dry powders. Many otherwise labile proteins and polypeptides may be stably stored as lyophilized or spray-dried powders by themselves or in combination with suitable powder carriers. The ability to deliver proteins and polypeptides as dry powders, however, is problematic in certain respects. The dosage of many protein and polypeptide drugs is often critical so it is necessary that any dry powder delivery system be able to accurately, and precisely (repeatably) deliver the intended amount of drug. Moreover, many proteins and polypeptides are quite expensive, typically being many times more costly than conventional drugs on a per-dose basis. Thus, the ability to efficiently deliver the dry powders to the target region of the lung with a minimal loss of drug is critical. It is further desirable that powder agglomerates present in the dry powder be sufficiently broken up prior to inhalation by the patient to assure effective systemic absorption or other pulmonary delivery.

A particularly promising approach for the pulmonary delivery of dry powder drugs utilizes a hand-held device with a pump or other source of pressurized gas. A selected amount of the pressurized gas is abruptly released through a powder dispersion device, such as a Venturi tube, and the dispersed powder made available for patient inhalation. While advantageous in many respects, such hand-held devices are problematic in a number of other respects. The particles being delivered are very fine, usually being sized in the range from 1 µm to 5 µm, making powder handling and dispersion difficult. The problems are exacerbated by the relatively small volumes of pressurized gas, typically 2 ml to 25 ml at 20 to 150 psig, which are available in such devices. In particular, Venturi tube dispersion devices are unsuitable for difficult-to-disperse powders when only small volumes of pressurized gas are available. Moreover, Venturi tube dispersion devices have very small powder inlet orifices which are easily plugged by the powders used for pulmonary delivery. Another requirement for hand-held and other powder delivery devices is high dosage concentration. It is important that the concentration of drug in the bolus of gas be relatively high to reduce the number of breaths and/or volume of each breath required to achieve a total dosage. The ability to achieve both adequate dispersion and small dispersed volumes is a significant technical challenge.

It would therefore be desirable to provide methods and systems for the dispersion of dry powder protein, polypeptide, and other drugs which meet some or all of the above objectives.

2. Description of the Background Art

Dry powder dispersion devices for medicaments are described in a number of patent documents. U.S. Pat. No. 3,921,637 describes a manual pump with needles for piercing through a single capsule of powdered medicine. The use of multiple receptacle disks or strips of medication is described in EP 467172 (where a reciprocatable piercing mechanism is used to piercing mechanism through opposed surfaces of a blister pack); WO91/02558; WO93/09832; WO94/08552; U.S. Pat. Nos. 4,627,432; 4,811,731; 5,035,237; 5,048,514; 4,446,862; and 3,425,600. Other patents which show puncturing of single medication capsules include U.S. Pat. Nos. 4,338,931; 3,991,761; 4,249,526; 4,069,819; 4,995,385; 4,889,114; and 4,884,565; and EP 468914.

WO90/07351 describes a hand-held pump device with a loose powder reservoir.

A dry powder sonic velocity disperser intended for industrial uses and very high flow rates is described in Witham and Gates, *Dry Dispersion with Sonic Velocity Nozzles*, presented at the Workshop on Dissemination Techniques for Smoke and Obscurants, Chemical Systems Laboratory, Aberdeen Proving Ground, Md., Mar. 14–16, 1983.

A pneumatic powder ejector having a suction stage and an injection stage is described in U.S. Pat. No. 4,807,814. The device comprises an axial gas Venturi tube and a lateral powder inlet.

Pittman and Mason (1986), Solids Handling Conference, Paper C4, pages C-41 to C-51, describes an ejector nozzle (FIG. 2) having an annular air inlet upstream of a venturi restriction.

SU 628930 (Abstract) describes a hand-held powder disperser having an axial air flow tube.

SU 1003926 (Abstract) describes a gas thermal coating injector.

Budrik and Zhelonkina (1978), "Ejector Feeders for Pneumatic Transport Systems," in *Chemical and Petroleum Engineering*, Consultants Bureau, New York, describes differing efficiencies in several ejector designs.

Zholob and Koval (1979), Poroshkovaya Metallurgiya 6:13–16, describes effects of injector design on particle size.

Bohnet (1984) "Calculation and Design of Gas/Solid-Injectors," in *Powder Technology*, pages 302–313, discusses conventional injector design.

Fox and Westaway (1988) Powder and Bulk Engineering, March 1988, pages 33–36, describes a venturi eductor having an axial air inlet tube upstream of a venturi restriction.

NL 7712041 (Abstract) discloses an ejector pump which creates suction and draws powder into a separator.

EP 347 779 describes a hand-held powder disperser having a collapsible expansion chamber.

EP 490 797 describes a hand-held powder disperser having a spring-loaded piston, where the piston carries a dispersion nozzle.

U.S. Pat. No. 3,994,421, describes a hand-held powder disperser having a collapsible deceleration chamber.

Pulmonary drug delivery is described in Byron and Patton (1994) J. Aerosol Med. 7:49–75.

SUMMARY OF THE INVENTION

The present invention provides methods and apparatus for efficient pulmonary delivery of accurate, precise, and repeatable dosages of powdered medicaments. The present invention will be particularly useful for the delivery of costly biopharmaceuticals such as protein, polypeptide and polynucleic acid drugs, but will also be useful for the systemic or localized delivery of any powdered medicament through the lungs. The delivery system and method produce substantially complete dispersion of the medicament powder with the break-up of any agglomerates of the powder which may have formed prior to delivery. The method and apparatus will find particular use in the dispersion of finely powdered medicaments from unit dosage receptacles, such as blister packs or cartridges, where the present invention is able to fluidize and extract substantially the entire amount of powder (usually at least 70% by weight, more usually at least 80%, and preferably at least 90%) within the receptacle, thus minimizing waste and enhancing the accuracy and precision of the dosage. The methods and approaches, however, will also find use with the dispersion and delivery of preselected metered amounts (boluses) of powdered medicaments from receptacles containing multiple dosage units, i.e. "bulk" powders contained in a single receptacle.

The methods and apparatus of the present invention are particularly suitable for the delivery of powders formed from discrete particles in the size range from 1 µm to 5 µm. Such powders, when properly dispersed in an aerosol, are optimum for delivery into the alveolar regions of the lung. However, they are particularly difficult to handle, and frequently become highly agglomerated during processing, packaging, and handling. Heretofore, handling characteristics of such powders have often been enhanced by combining the fine drug particles with larger carrier particles which have easier handling and dispersion characteristics. Use of a carrier, however, dilutes the drug, requiring a larger dispersion volume for a given drug dosage. The carrier particles can also cause choking when inhaled and serve no purpose other than improving handling characteristics. The present invention is able to achieve dispersion of fine drug particles with little or no carrier substances by a two-step dispersion method. The present invention, however, will be functional with drug compositions which include such carrier particles, as well as with diluents which may be necessary to achieve desired dosage concentrations.

The powders are first fluidized within the receptacle, as described above, resulting in fluidized particles and particle agglomerates which are then dispersed in the high velocity gas stream under conditions which break up such agglomerates. Such complete dispersion can be achieved with very low volumes of high velocity air and fluidization air, resulting in a well dispersed drug bolus having relatively high drug particle concentrations. Of course, the present invention is useful as well with drug formulations including a carrier diluent, or the like. The advantage of the present invention is that the use of carriers can often be reduced or eliminated altogether.

According to the method of the present invention, the powdered medicament is contained in a receptacle having a puncturable lid or other access surface. A powder inlet end of a feed tube is coupled with, i.e. engaged against or inserted through, a penetration in the access surface, and a high velocity airstream (usually sonic which provides sufficient shear forces to separate agglomerates into individual particles) is flowed past a portion of the tube, such as an outlet end, to draw powder from the receptacle, through the tube, and into the flowing airstream to form the desired aerosol. Usually, at least two spaced-apart discrete penetrations will be formed in the access surface prior to coupling the inlet end of the feed tube with one of the penetrations. The other penetration permits a separate stream of fluidization air to enter the receptacle, fluidize the powder, and sweep the receptacle of the fluidized powder to help assure that substantially all powder (preferably at least 70%, more preferably at least 80%, and still more preferably at least 90%) is removed into the flowing air stream. The high pressure gas stream will be generated by abruptly releasing a charge of pressurized gas through a flow path which intersects with the outlet end of the feed tube at an angle selected to both (1) induce sufficient fluidization air flow through the feed tube to fluidize and transport powder in the receptacle and (2) break up powder agglomerates which remain as the powder exits from the outlet end of the feed tube. The gas pressure prior to release will usually be at least about 15 psig (to achieve sonic velocity), preferably being at least 20 psig, and more preferably being in the range from 20 psig to 150 psig, and usually being in the range from 40 psig to 80 psig. The expanded volume of released gas (measured at standard temperature and pressure (STP) of 14.7 psig and 20° C.) will thus usually be in the range from 2 ml to 25 ml, preferably being from 4 ml to 15 ml. Release of the high pressure gas can be effected by a manual trigger or optionally by sensing negative pressure resulting from the patient's inspiration (i.e., can be breath-activated). As described in detail below, the high pressure gas stream will combine with the fluidization air stream at a volume ratio (measured at STP) in the range from 1:2 to 1:4 (high pressure gas: fluidization air) to produce the aerosol which is subsequently inhaled by the patient, optionally after capture in a plume capture chamber.

The method may further comprise the step of capturing the resulting discrete volume of aerosolized powder in a plume capture chamber prior to subsequent inhalation by the patient. The patient is then able to inhale the entire aerosolized dose from the chamber, concurrently with and/or followed by inhalation of ambient air which sweeps the capture chamber to further assure efficient delivery of the powder with minimum losses. Inhalation of chase air following the initial bolus of medication will drive the medication deep into the alveolar regions of the lung where absorption will occur. The method optionally further comprises advancing a plurality of powder-containing receptacles past the feed tube, typically in the form of a strip or disk, so the powder can be sequentially drawn and dispersed from each receptacle.

In another aspect of the method of the present invention, discrete quantities of a powdered medicament may be sequentially delivered from a receptacle or reservoir. In contrast with the previously described methods, the receptacle will include an amount of powdered medicament which is larger than that intended to be delivered in any single bolus, usually containing an amount which is sufficient for a large number of boluses, usually at least 5, preferably at least 10, and frequently 20 or more. The method comprises inserting the inlet end of the feed tube into the receptacle and flowing a high pressure gas stream past an outlet end of the feed tube to induce airflow from the receptacle through the tube. The powdered medicament is thus entrained in the airflow passing through the feed tube and combined with the high pressure gas stream at an outlet end of the feed tube. The high pressure gas stream can be repeatedly directed past the outlet end of the feed tube while the inlet end remains within the "bulk" powdered medicament receptacle.

Apparatus according to the present invention comprise a base enclosure having a support for the powder-containing receptacle at a fluidization location. The feed tube is mounted within the base enclosure and a mechanism for reciprocating the receptacle relative to the feed tube (or extending the feed tube relative to the receptacle) is optionally provided. A source of compressed gas for generating the high pressure gas is also provided, typically in the form of a hand-actuated pump, an electric (usually battery-operated) pump, a compressed gas container, a two-fluid system, or the like. The aerosolized powder dosage may thus be formed by reciprocating the receptacle relative to the feed tube so that the inlet end of the tube enters the receptacle. The high pressure gas stream is released while the tube is in or adjacent to the receptacle, and the resulting low pressure region at the outlet end of the feed tube draws fluidization air into the receptacle (preferably from the plume capture chamber which subsequently receives the aerosol, thus minimizing net air introduced from outside the device) to fluidize and extract the powder outward from the receptacle through the tube, and into the high velocity gas stream to form the desired dispersion. Usually, the capture chamber is disposed over and in-line with the outlet end of the feed tube to contain the "plume" of powder aerosol and allow the plume to quiesce prior to inhalation by the patient. The feed tube does not have nozzles or ejector tubes within the flow path, and the clear, straight flow path reduces any tendency for the feed tube to clog or otherwise lose dispersion efficiency. Using air from the capture chamber as a source of fluidization gas is advantageous since it reduces the total volume of "new" gas introduced to the chamber, making capture of the dispersion gas stream (i.e., the combination of the high pressure gas stream and the fluidization air stream) easier. Such recycling of air from the capture chamber, however, is not an essential feature of the present invention. Fluidization air can also be obtained directly from outside the device.

In a preferred aspect of the apparatus of the present invention, the receptacle will be supported in a mechanism for advancing a continuous web (e.g. a strip or disk) which carries a plurality of receptacles past the fluidization location. Usually, the web advance mechanism includes a cartridge or carriage which holds the web and which is reciprocatably mounted relative to the feed tube so that the receptacles may be sequentially advanced while the cartridge and tube are separated, and the tube thereafter introduced into the receptacle by moving the cartridge and tube together. Optionally, the receptacle lid or other single access surface (i.e., a surface on one side of the receptacle) will be pierced immediately prior to introduction of the feed tube, usually using a separate piercing mechanism which pierces the lid as the cartridge is reciprocated relative to the feed tube. Alternatively, the access surface can be pierced simultaneously with the insertion of the feed tube. In the latter case, the inlet end of the feed tube will usually have a piercing structure and/or additional piercing structures will be provided to form additional penetrations for the entry of the fluidization air.

In a specific aspect of the apparatus of the present invention, the piercing mechanism will produce at least two spaced-apart holes in the lid, where one hole receives or engages the feed tube and the other hole(s) permit entry of displacement air to fluidize the powder and sweep the receptacle as powder is withdrawn through the feed tube. A conduit or other path may also be provided for directing air from the plume capture chamber back to the receptacle in order to at least partially provide the necessary displacement air. The hole for the feed tube may be formed simultaneously with or at a different time from the displacement air hole(s). For example, the displacement air hole(s) could be formed at a piercing station disposed ahead of the dispersion station with the feed tube formed at the dispersion station, or vice versa. It also may be desirable to provide a piercing mechanism at the dispersion station where the feed tube piercing structure is reciprocated relative to the receptacle in a separate motion from the displacement air hole piercing structure.

The present invention further provides apparatus for aerosolizing of powder comprising a feed tube having an inlet end, an outlet end, and a lumen defining an axial flow path between said inlet end and outlet end. At least one conduit is provided for flowing a high velocity gas stream past the outlet end in a direction which converges with the axial flow path at an angle in the range from 12.5° to 65°. It has been found that the angle of convergence in this range induces a sufficient flow of fluidization air in the feed tube to efficiently empty an associated powder receptacle (typically removing and aerosolizing at least 80% and preferably at least 90% of the powder initially present in the receptacle) while also providing sufficient shear energy at the outlet end to substantially break up agglomerates which are present in the powder.

The aerosolizing apparatus may include two or more separate gas conduits which converge from different, usually opposite (diametrically opposed), sides of the flow path. Alternatively, the high pressure gas conduit may terminate in a single annular aperture which circumscribes the outlet end of the feed tube and which creates a gas flow path which converges on the axial flow path. The latter approach however, will generally be less preferred since it is difficult to manufacture annular apertures in the small size required. The total lumen area ($A_1$) of the high pressure (dispersion) gas flow conduit(s) will usually be in the range from 0.05 mm$^2$ to 0.3 mm$^2$, while the throat of the feed tube immediately upstream of the gas conduit(s) tube will have a lumen area ($A_2$) in the range from 0.5 mm$^2$ to 10 mm$^2$. The area ($A_3$) and length of the mixing volume immediately downstream from the high velocity gas conduits are preferably in the range from the 0.6 mm$^2$ to 11 mm$^2$ and 0.5 mm to 3 mm, respectively. The feed tube upstream of the throat will usually have an area ($A_4$) in the range from 0.6 mm$^2$ to 15 mm$^2$.

The aerosolizing apparatus may further include a diffuser tube extending from the outlet end of the mixing volume and having a lumen which is usually but not necessarily coaxially aligned with the feed tube lumen. The diameter of the diffuser tube lumen will increase in a direction away from the outlet end of the mixing volume, typically diverging at a half angle of 2° to 10° over a length in the range from 0.5 cm to 5 cm, usually having an outlet area which is about four times the inlet (mixing volume) area. The diffuser tube thus causes a reduction in the velocity of the gas stream exhausted from the outlet end of the mixing volume, where velocity is at a maximum, prior to entering the plume capture chamber. The plume continues to slow rapidly as it expands within the chamber and approaches a quiet or quiescent state prior to inhalation.

The present invention further provides a feed tube assembly comprising a casing, a flow-directing member, and a feed tube. The assembly is replaceable within the aerosol dispersion system, facilitating removal and cleaning or exchange of the assembly when it becomes plugged or fouled.

BRIEF DESCRIPTION OF THE DRAWINGS

FIG. 1 is a schematic illustration of an aerosol dispersion system constructed in accordance with the principles of the present invention.

FIG. 2 is a perspective illustration of a powder feed tube assembly employed in the aerosol dispersion system of FIG. 1, shown in quarter-section with its inlet end proximate a powder receptacle.

FIG. 3 illustrates a preferred powder receptacle lid penetration pattern.

FIG. 4A is a cross-sectional view of a portion of the feed tube assembly illustrated in FIG. 2.

FIG. 4B is a cross-sectional view taken along line 4B—4B of FIG. 4A.

FIG. 4C is an alternative cross-sectional view taken along line 4B—4B of FIG. 4A.

FIG. 5 is a schematic illustration showing the relative sizes and convergence angles of the feed tube lumen and dispersion gas conduits of the present invention.

FIG. 6 illustrates a feed tube lumen in combination with a dispersion gas conduit having an annular aperture which defines a conical flow path.

FIG. 7 is a perspective view of an alternative feed tube assembly constructed in accordance with the principles of the present invention.

FIG. 8 is an exploded view of the feed tube assembly of FIG. 7.

FIG. 9 is a cross-sectional view of the feed tube assembly of FIG. 7

FIG. 10 illustrates a third alternative feed tube assembly, similar to that of FIG. 7–9, but further including self-penetrating elements which permits entry of the feed tube and fluidization air tubes into a powdered medicament receptacle.

FIG. 11A is an enlarged, detailed view of the self-penetrating elements of FIG. 10.

FIG. 11B is an enlarged view of an alternative construction of a self-penetrating element.

FIGS. 12A–12C illustrate use of the feed tube assembly of FIGS. 7–9 in dispersing a powdered medicament from a single unit dosage receptacle.

DESCRIPTION OF THE SPECIFIC EMBODIMENT

Referring now to FIG. 1, a system 10 for dispersing a powder medicament from a plurality of receptacles 12 by insertion of a feed tube assembly 14 will be described. The receptacles may be in any form that holds and preserves the medicaments and which provides a puncturable access surface. As illustrated, receptacles 12 are in a continuous web comprising individual wells covered by a puncturable lid, typically a metal foil or other conventional laminate. Each receptacle will include a precise dosage of the powdered medicament to be delivered. The amount of powder in each individual receptacle will usually be in the range from about 1 mg to 20 mg, more usually being from 2 mg to 10 mg. The continuous web may be in the form of a strip, disk, or molded structure with a closure. The manufacture of such containers, often referred to as "blister packs" is well known in the pharmaceutical packaging art and need not be described further.

Although illustrated with cartridge 22 in FIG. 1, it will be appreciated that the powder dispersion systems of the present invention could also be constructed to receive single dosage packages carrying only one receptacle. In such a case, the user would insert the package so that the receptacle was properly oriented relative to feed tube 40 (FIG. 2) of feed tube assembly 14. Necessary piercings in the access surface of the receptacle could be made manually prior to insertion, could be made within the system 10 (either prior to or simultaneous with introduction of the feed tube assembly 14) or could be preformed and exposed by peeling away a cover prior to insertion of the package into the device. Multiple receptacle packages could also be provided where the package is inserted into the device at different orientations in order to selectively expose individual receptacles to the feed tube. A variety of design options are available when the user inserts a single receptacle prior to each use.

The system 10 further comprises a base enclosure 11, and the feed tube 40 (FIG. 2) of feed tube assembly 14 has an inlet end 16 and an outlet end 18. A pressurized gas source 20 is provided within the base enclosure 11 and is connected to the proximal end of the feed tube assembly 14 to provide a high pressure gas stream, as will be described in greater detail in connection with FIG. 2.

The receptacles 12 will be mounted within the base enclosure 11 to reciprocate relative to the inlet end 16 of feed tube assembly 14. Preferably, the strip of receptacles 12 will be mounted within a cartridge 22 which is reciprocatably mounted in the base enclosure 11, while the feed tube assembly 14 is fixedly mounted within the base enclosure. In this way, the receptacles 12 may be sequentially advanced past a fluidization location (defined by the inlet end 16 of feed tube assembly 14) within the cartridge 22, with the receptacle which is at the dispersion or fluidization location being brought proximate the inlet end 16 of the feed tube to permit emptying of its powdered contents, as described in more detail hereinafter. Both reciprocation of the cartridge 22, and advance of the receptacles 12 within the cartridge, may be accomplished manually by the user. Alternatively, a mechanism may be provided within the base enclosure 11 for simultaneously reciprocating the cartridge 22 and advancing the strip of receptacles 12, either as part of a manual advance mechanism or as part of a battery-powered mechanism.

In the embodiment of FIG. 1, penetrations will be formed in the lid of the strip of receptacles 12 by a piercing mechanism 24. As illustrated, the piercing mechanism 24 will be fixedly mounted within the base enclosure 11 and will include a plurality of sharpened penetrating elements 26 disposed to contact and penetrate the puncturable lid 92 (FIG. 3) of the receptacles 12 when the cartridge 22 is reciprocated, as illustrated in broken line in FIG. 1. The piercing mechanism 24 will be located to contact a receptacle 12 which is located one station prior to the feed tube assembly 14. Thus, each receptacle 12 will be pierced immediately prior to being advanced to the fluidization location.

It will be appreciated that a wide variety of mechanisms can be provided for piercing holes within the lid of each receptacle and for bringing the receptacle into proximity with the feed tube assembly 14. For example, the cartridge 22 could be held stationary within the base enclosure 11 while each of the feed tube assembly 14 and piercing mechanism 24 could be reciprocated, either together or separately. Alternatively, the inlet end 16 of the feed tube assembly 14 could be configured to be self-penetrating (see FIGS. 10 and 11A and 11B below). In the latter case, the desired pattern of penetrations would be formed in the puncturable lid of the receptacle 12 at the same time that the inlet end is engaged against or inserted into the interior of the receptacle. The present invention is not limited to any particular puncturing and advance mechanisms which might be employed.

The gas source 20 will provide a volume of high pressure air or other gas to the outlet end 18 of the feed tube 40 (FIG. 2) of feed tube assembly 14 in order to induce a flow of fluidization air, draw powder from the receptacles 12, and disperse the powder within the flowing gas stream. While the high velocity air from the gas source will usually be directed past the outlet end 18, it will be appreciated that feed tube 40 could be extended past the high velocity gas stream inlet point, for example by providing side inlets in an elongate tube. Thus, the high velocity gas could actually combine with the fluidization air carrying the entrained particles within the feed tube itself. With such a construction, the feed tube 40 could define the mixing volume 60 (FIG. 4A), as described below.

The gas source 20 will provide gas at a relatively high pressure, usually being sufficient to provide for sonic flow past the outlet end 18 of the feed tube assembly 14, typically being above 15 psig, usually being at least 20 psig, and preferably being in the range from 20 psig to 150 psig. The energy stored in the charge of high pressure gas will be sufficient to induce air flow through the feed tube 40 of feed tube assembly 14 which in turn draws fluidization air into the receptacle to fluidize and extract the expected weight of powdered medicament from the receptacle 12. The expanded volume of the charge will typically be in the range from about 2 ml to 25 ml (measured at STP), usually being in the range from about 4 ml to 15 ml. The volume of fluidization gas whose flow is induced through the feed tube assembly 14 by the high velocity gas stream will usually be from 2 ml to 100 ml, preferably from 4 ml to 60 ml, measured at STP. The specific manner in which the high pressure gas is flowed past the outlet end 18 of feed tube assembly 14 will be described in greater detail in connection with FIG. 2.

Gas source 20 may be in the form of a manual pump, an electric pump, a high pressure gas cylinder, or the like. The construction of manual pumps in hand-held powder dispersion devices is described in the patent and technical literature. See e.g., WO90/07351. The construction of electric gas pumps, gas cylinder supplies, and two-fluid systems is also well within the skill in the art.

The gas dispersion system 10 further includes a plume capture chamber 30 which is disposed over the outlet end 18 of feed tube assembly 14 in order to capture powder released from the tube. The plume chamber 30 will include a mouthpiece 32 at its distal end and will have an internal volume sufficient to capture substantially all of the powder dispersion which is delivered from the feed tube assembly 14. Usually, the volume will be in the range from 50 ml to 1000 ml, preferably from 100 ml to 750 ml. The chamber 30 will also include an ambient air inlet (not shown), optionally a tangential inlet as described in co-pending application Ser. No. 07/910,048, the full disclosure of which is incorporated herein by reference. Alternatively, the air inlet can be axial or spiral, as described in connection with FIGS. 7–9, below.

In operation, the powder dispersion will be introduced into the plume capture chamber 30, as illustrated by arrows 34. Air will be displaced through the mouthpiece 32, and optionally back through an annular lumen in the feed tube assembly 14, as indicated by arrows 36 and as will be described in more detail in connection with FIG. 2. Such recycling of air from the plume capture chamber 30 as the fluidization gas greatly reduces the total volume of new gas being introduced to the system. The only new gas introduced (prior to patient inhalation) will be from the gas source 20. After the entire contents of a receptacle 12 has been dispersed and captured within the plume chamber 30, the patient will inhale the entire aerosolized dose through the mouthpiece 32 chased by ambient air through the chamber to extract all aerosolized medicament from the chamber. Optionally, an orifice plate or other flow limiting element may be placed in the chamber air inlet path to slow inhalation and enhance the penetration depth of the powder particles. Inhalation of the additional air further assures that the powdered medicament will be efficiently dispersed and driven deeply into the alveolar regions of the lung where it is available for systemic absorption or localized delivery.

Figure 2:
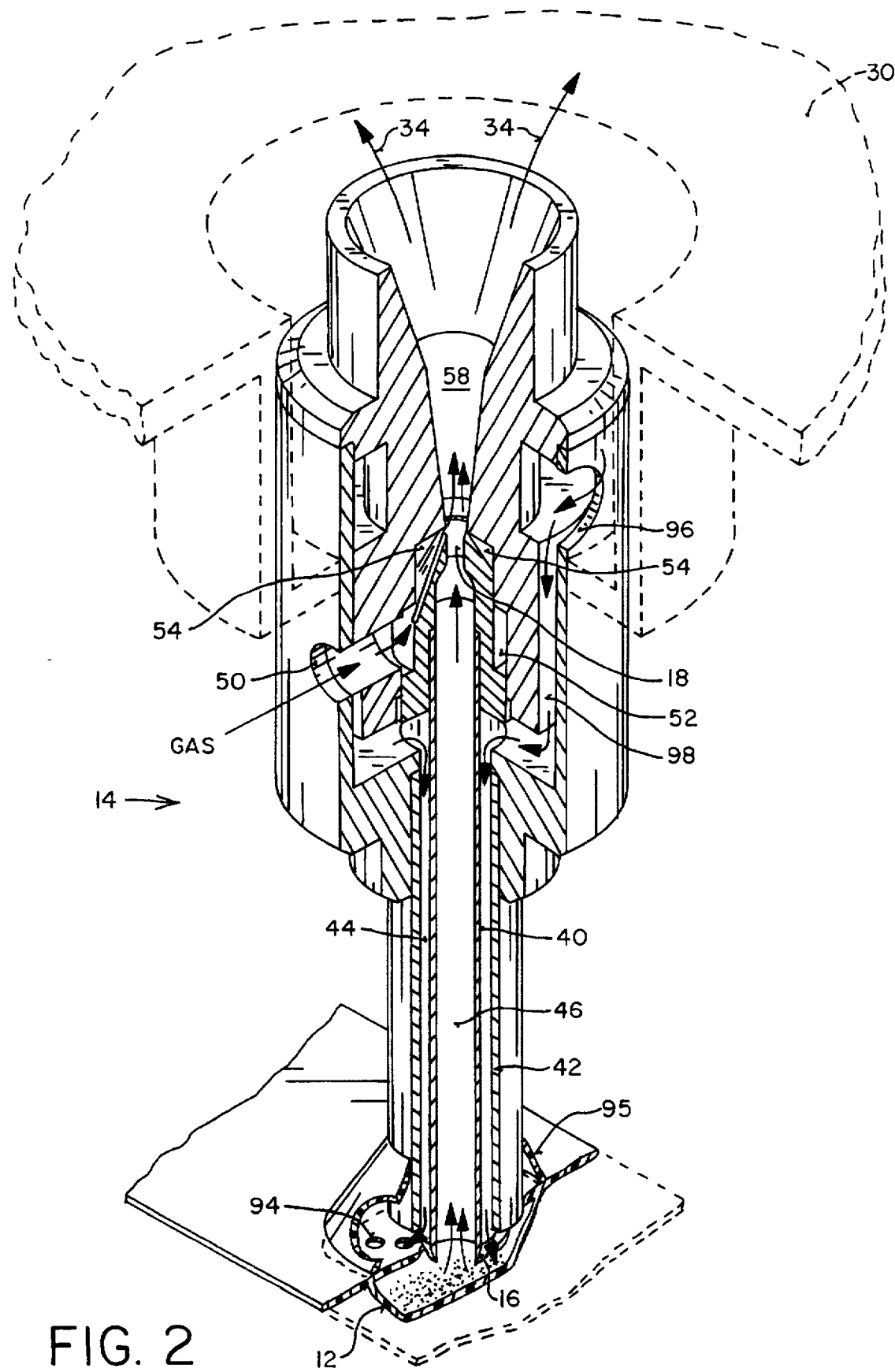

Referring now to FIG. 2, the feed tube assembly 14 includes an inner tubular feed tube 40 which defines the inlet end 16 of the feed tube assembly 14 at its distal end and an outer coaxial tube member 42 which defines an annular lumen 44 for passing return air from chamber 30 back to the receptacle 12, as described in more detail hereinafter.

Lumen 46 of the inner tubular feed tube 40 extends from the inlet end 16 to the outlet end 18 where a throat or constriction is optionally formed. The throat or constriction is not necessary for operation of the feed tube assembly 14, but it is the area ($A_2$) at the outlet end of the lumen 46 (FIG. 4A) which determines the performance characteristics of the feed tube, as described in more detail hereinafter. Dispersion gas from gas source 20 enters the feed tube assembly 14 through a port 50 connected to an annular plenum 52. The annular plenum 52, in turn, is connected to a pair of gas conduits 54 which direct converging gas streams into the flow path defined by lumen 46 of the feed tube 40. The angle at which the gas conduits 54 are oriented is chosen to provide a proper balance between the magnitude of the flow velocity induced in the powder stream drawn through lumen 46 and the magnitude of the shear forces which break up agglomerates in the powder as they pass from the outlet end 18 into an expansion section (or diffuser tube) 58.

The area ($A_2$) (FIG. 4A) of the throat 18 of the feed tube lumen 46 will typically be in the range from 0.5 mm$^2$ to 10 mm$^2$, preferably being in the range from 1 mm$^2$ to 4 mM$^2$. In the illustrated embodiment, area ($A_4$) of the upstream portion of lumen 46 (FIG. 4A) is greater than $A_2$, typically being from 0.6 mm$^2$ to 15 mm$^2$. The upstream lumen 46, however, could have a uniform area along its entire length equal to the outlet end area ($A_2$), although such a construction would be less preferred.

Figures 3, 4A, 4B, 4C:
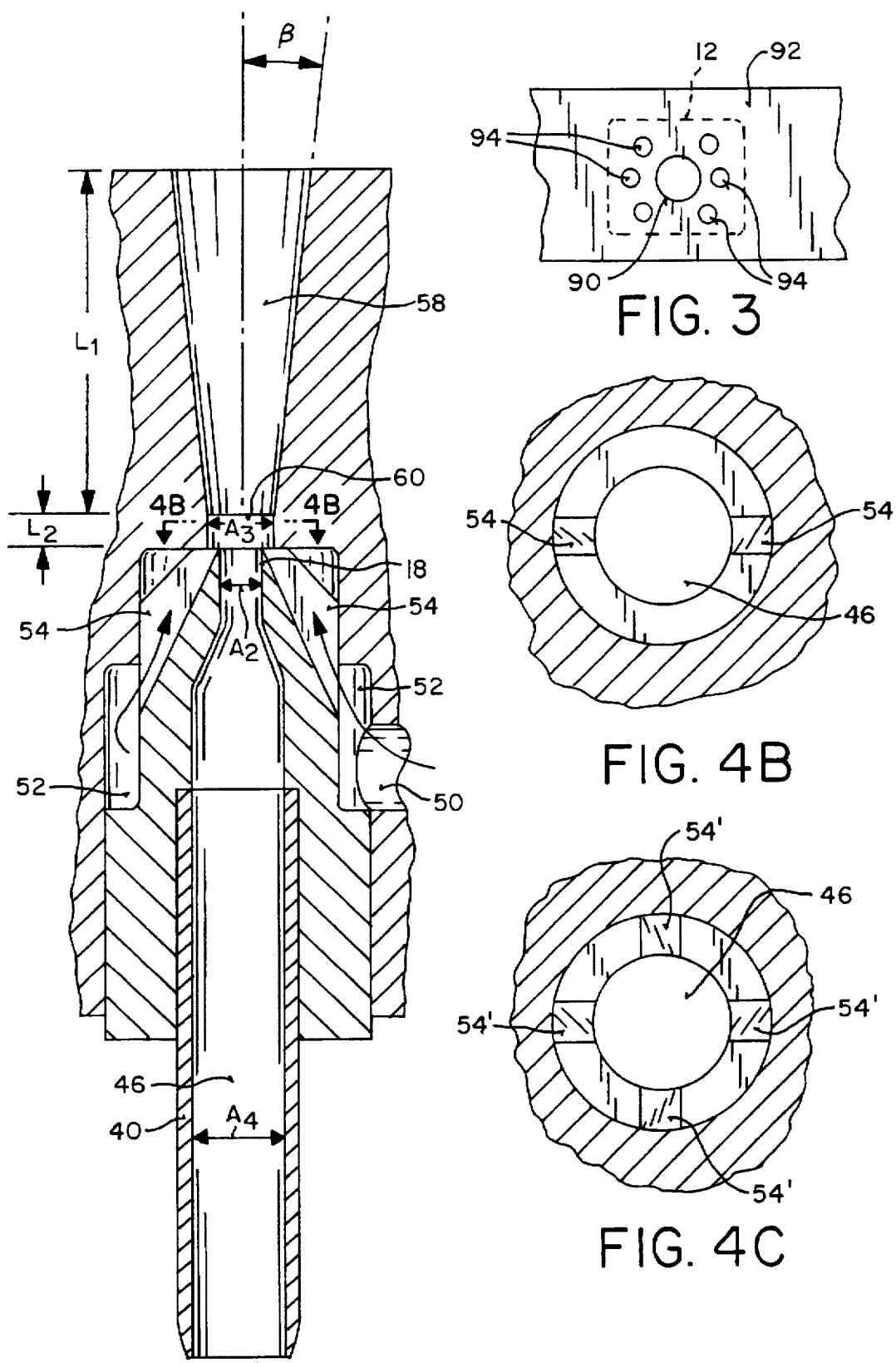

Referring to FIG. 4A, a mixing volume 60 having a uniform (non-expanding) cross-sectional area ($A_3$) and a length ($L_2$) is located immediately at the outlet end 18 of the feed tube 40. The cross-sectional area ($A_3$) is shown to be slightly larger than feed tube throat area($A_2$) outlet, but this is not necessary. The exemplary area($A_3$) is typically in the range from 0.6 mm$^2$ to 11 mm$^2$. The length ($L_2$) is 1–5 times the diameter of the mixing volume 60 (for circular cross-sections), typically being in the range from 0.5 mm to 2 mm. In the illustrated embodiment, a pair of gas conduits 54 (FIG. 4B) are shown, as illustrated in FIG. 4B. It would also be possible to utilize only a single inlet jet or to provide three, four or more separate inlets, with four inlets 54' being as illustrated in FIG. 4C. Other configurations will also be usable including a continuous annular aperture, as described in connection with FIG. 6, or combinations of perpendicular jets (to break-up agglomerates) and axially directed jets (to induce fluidization gas flow).

Figure 5:
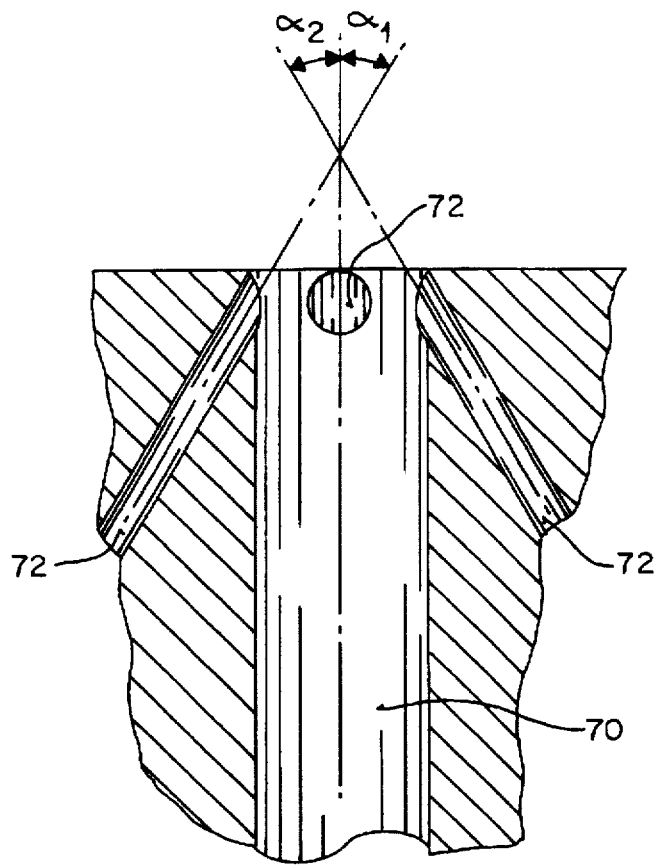

Referring now to FIG. 5, high pressure gas conduits 72 are arranged around the throat of a feed tube lumen 70 at angles $\alpha_1$ and $\alpha_2$, which will usually but not necessarily be equal. The angles α are important to achieving both adequate mass transfer of powder from the receptacle and adequate "agglomerate break up" as the powder enters the mixing volume immediately downstream from the outlet orifices of the conduits 72. The angles a will be in the range from 12.5° to 65°, preferably being from 25° to 40°.

Figure 6:
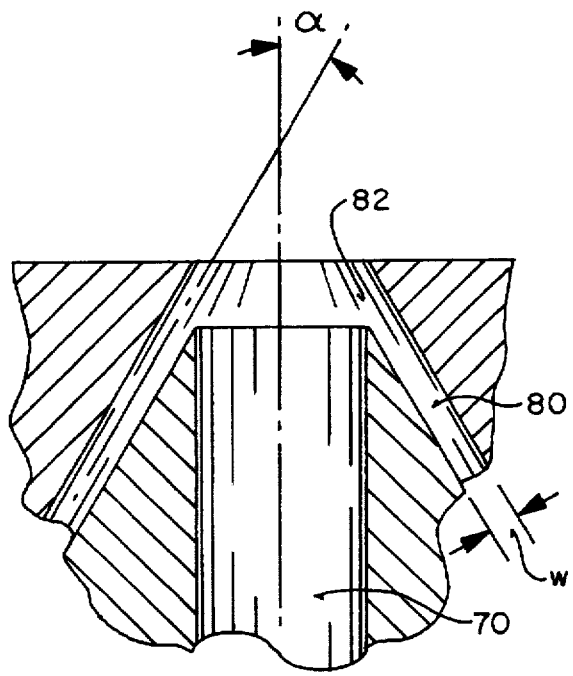

It will be appreciated that the high pressure gas lumens 72, as illustrated in FIG. 5, may be formed as a single conical plenum 80 terminating in an annular aperture 82, as illustrated in FIG. 6. The angle of convergence α will generally be within the range set forth above for α above, and the total area of the annular lumen 82 will generally be within the total area $A_2$ for the high pressure gas lumens also set forth above. Typically, the conical plenum 80 will have a width w in the range from about 0.005 mm to 0.1 mm.

Referring again to FIG. 2, the feed tube assembly 14 operates by coupling the inlet end 16 of the feed tube 40 with an aperture 90 (FIG. 3) formed into lid 92 over a receptacle 12. As illustrated, the inlet end 16 is inserted through the lid 92 and into the receptacle 12, but is will also be feasible to engage the inlet end over the aperture 90, typically utilizing a sealing gasket as illustrated in FIGS. 7–10, below. The aperture 90 will be surrounded by space-apart apertures 94 (illustrated as six) which allow for the entry of fluidizing air as entrained powder is extracted through the inner feed tube 40. The aperture 90 is shown to be centered, but that is not necessary. In a preferred aspect of the present invention, at least a portion (and preferably all) of the fluidizing air will be provided through the annular lumen 44 via a port 96 in the feed tube assembly 14 disposal at the bottom of the interior of the plume chamber 30. Such "recycled" air from the plume chamber 30 passes through an annular plenum 98 from the port 96 into the annular lumen 44. Optionally, a rubber flange or skirt 95 may be provided to prevent loss of fluidizing air from the lumen 44 to the receptacle 12. The recycling of fluidization air from the plume chamber 30 helps contain the plume of dispersed powder within the plume chamber since it limits the amount of air which is displaced and expelled through the mouthpiece 32 or other opening in the chamber.

Introduction of the inlet end 16 of feed tube 40 of the feed tube assembly 14 into the receptacle 12 is advantageous (but not necessary) since it facilitates substantially complete removal of powder (usually at least 80% and preferably at least 90% by weight) from the interior of the receptacle. Such complete removal is further enhanced by the entry of fluidization air through the space-apart apertures 94, which creates an air flow pattern which can sweep powder from all corners of the receptacle into the dispersion lumen 46.

Figure 7:
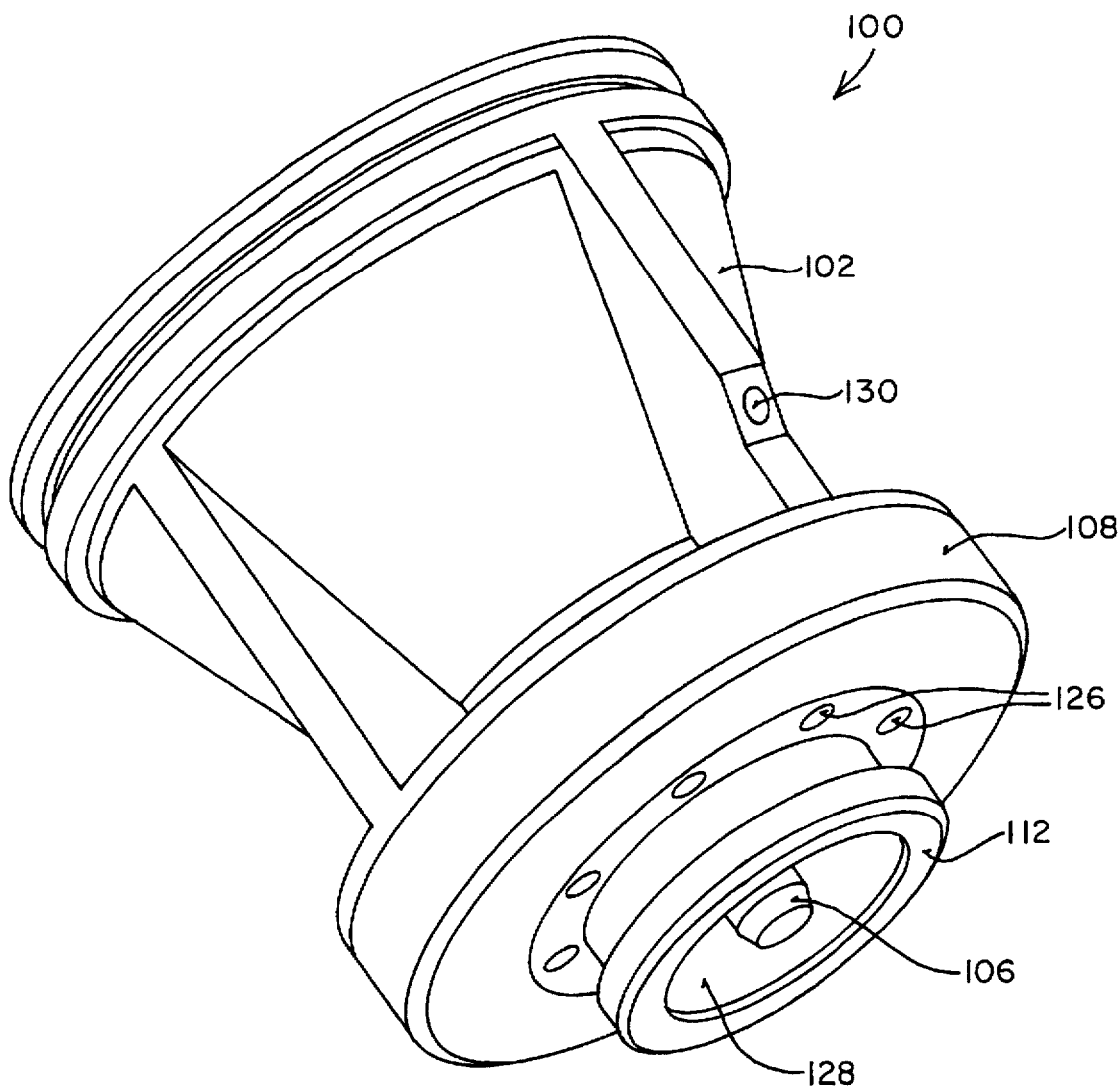
Figure 8:
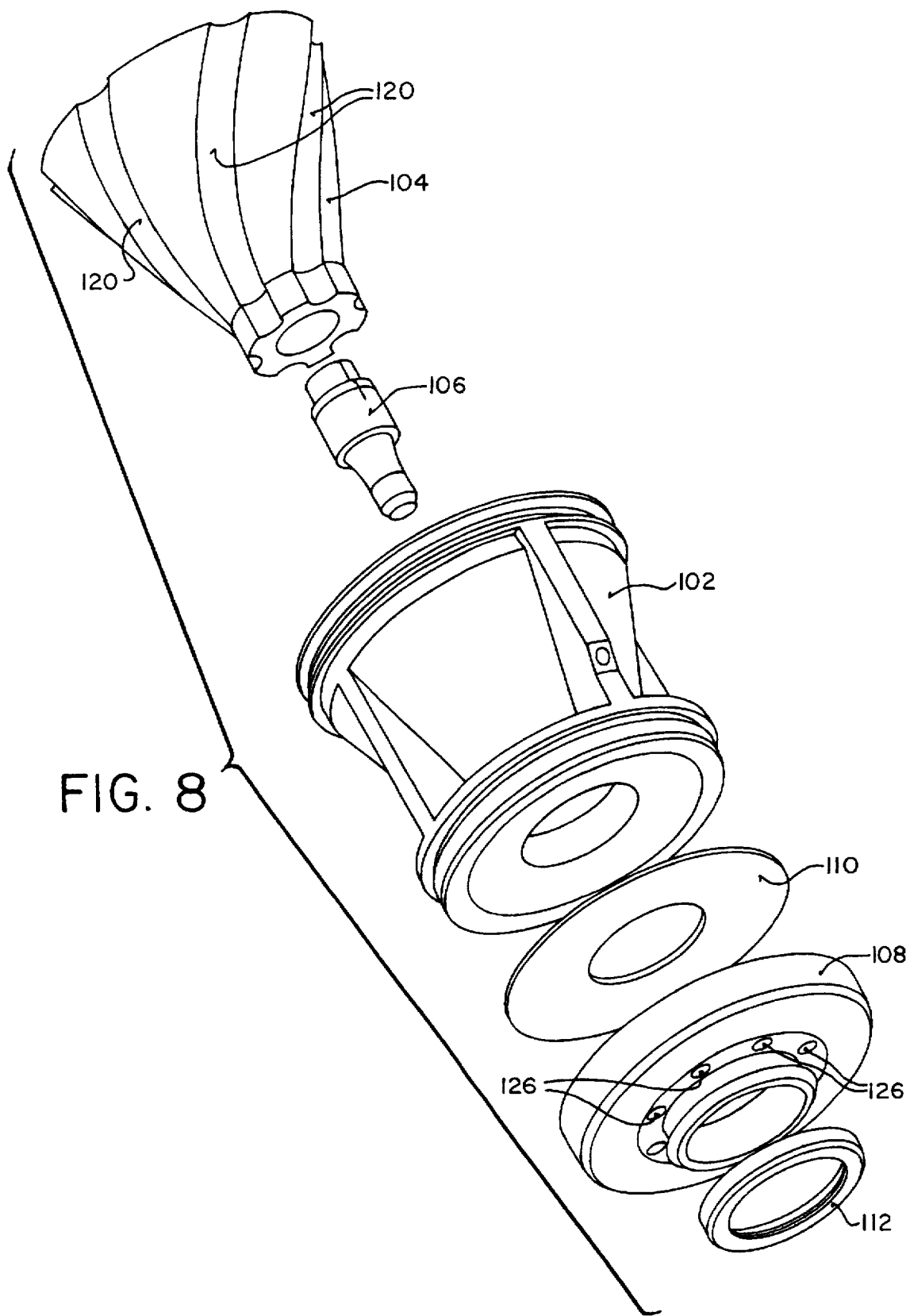
Figure 9:
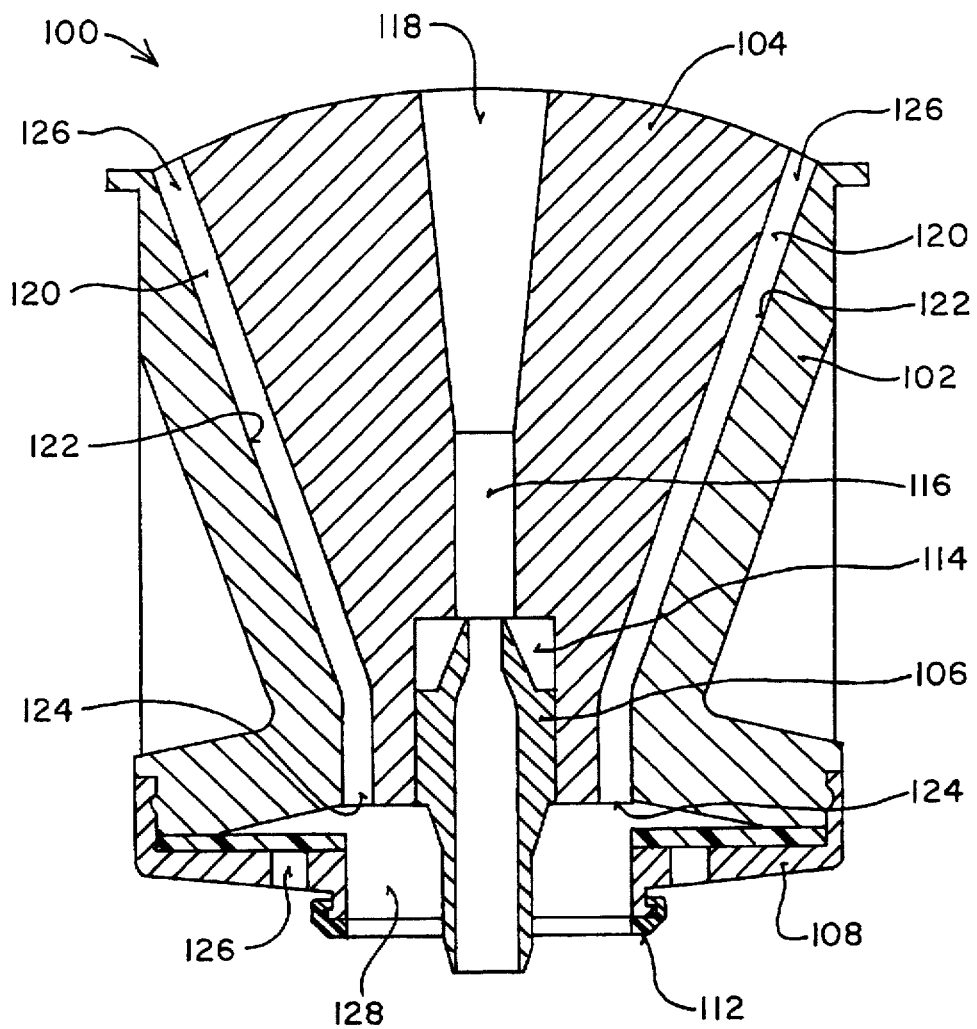

An alternative embodiment of a feed tube assembly 100 is shown in FIGS. 7–9. The feed tube assembly 100 is generally functionally equivalent to the feed tube assembly 14 and can be used in place thereof in the system of FIG. 1. The feed tube 100, however, is particularly suitable for fabrication from molded plastic parts, or from a combination of molded plastic and machined metal parts.

Feed tube assembly 100 comprises a casing 102, a gas flow-directing cone 104, a feed tube element 106, an end piece 108, a flexible valve element 110, and an end gasket 112. The feed tube element 106 is received in an open cavity 114 disposed in a lower end of the flow-directing cone 104. The flow passages within feed tube 106 will generally be the same as that described previously for feed tube assembly 14, and feed tube assembly 100 further includes a mixing volume 116 located immediately above the open cavity 114 and an expansion region 118 located above the mixing volume. The dimensions of the mixing volume 116 and expansion region 118 will generally be the same as those described previously in connection with the feed tube assembly 14.

As best seen in FIG. 8, the flow directing cone 104 may include a plurality of air flow channels 120 formed over its exterior surface. Usually, there will be from 1 to 10 channels, having a total cross-sectional area from 5 mm$^2$ to 150 mm$^2$, preferably from 40 mm$^2$ to 100 mm$^2$. The air flow channels 120 are shown in a generally spiral pattern in FIG. 8. The spiral pattern may be preferred since it will impart a vortical flow to replacement air entering the associated plume chamber as the patient inhales. The airflow channels 120, however, could also have a generally straight configuration which would impart a conically expanding, but not spiral, flow pattern to the replacement air. It would also be possible to employ air flow channels which are straight and parallel to each other to impart a general axial replacement airflow pattern into the plume chamber. It will also be possible to employ a single annular opening by using pins of other non-dividing elements for supporting the flow-direction cone, where the cone may have a continuous surface without discrete channels.

The airflow channels 120 are enclosed at their outward extremities by the inner surface 122 (FIG. 9) of the casing 102. The air flow channels thus extend from a lower end 124 to an upper end 126, providing flow paths for replacement or "chase" air into a plume chamber, as described in more detail below. The flow paths provided by air channels 120 will also provide for recycling of air in the reverse direction from the plume chamber to an associated powder receptacle when the powder is being fluidized. This function will be described in more detail below.

The end piece 108 includes a plurality of air flow apertures 126 located around a central opening 128. The flexible valve 110 lies over the air flow apertures 126 and is secured between the lower end of casing 102 and the upper surface of the end piece, as best seen in FIG. 9. The flexible valve element 110 generally acts a one-way valve, permitting entry of air from the outside of the feed tube assembly 100 into the region formed between the lower end of casing 102 and the end piece 108.

High pressure air will be able to enter the open cavity 114 formed at the outlet end of feed tube element 106 through an inlet port 130 formed in the casing 102 (FIG. 7). For simplicity, the flow path from port 130 to the cavity 114 is not shown in FIG. 9. Supply of high pressure gas to the cavity 114 acts to induce the flow of fluidization air through the central lumen of the feed tube element 106 in a manner completely analogous to that described previously for feed tube assembly 14.

Figure 10:
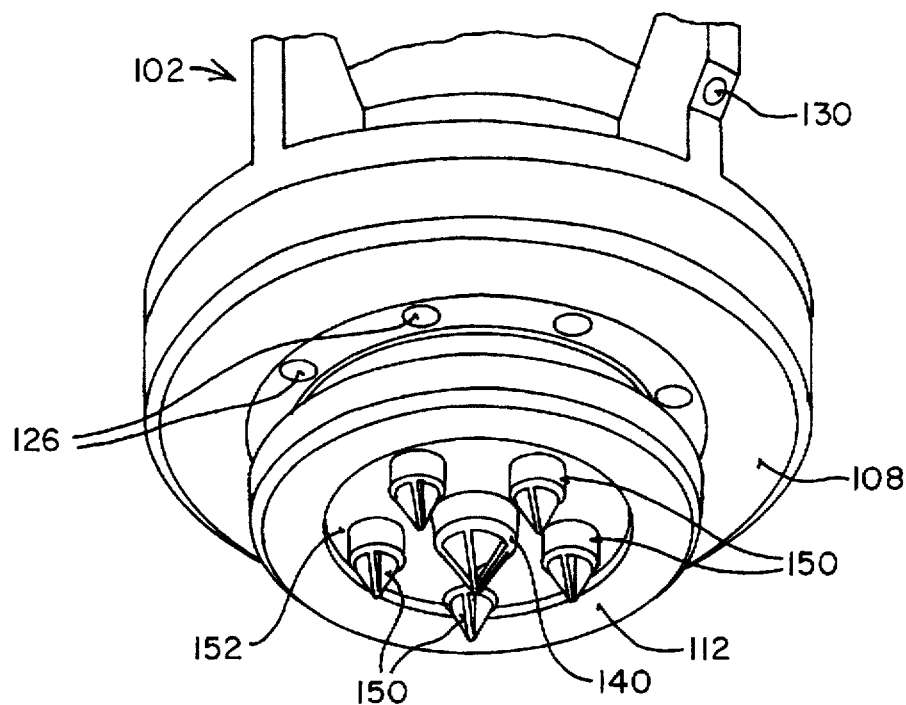
Figures 11A, 11B:
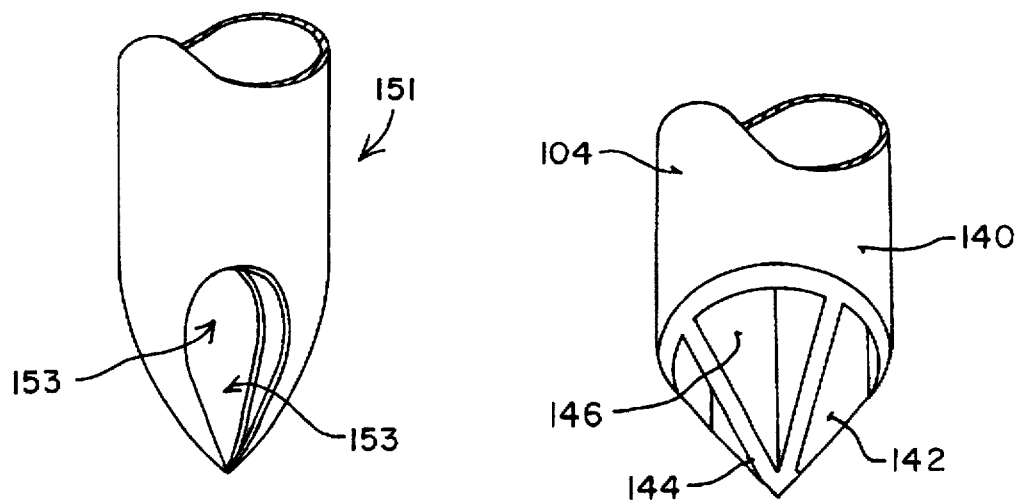

Referring now to FIGS. 10 and 11A, a modification of the feed tube assembly 100 which permits direct penetration of a medicament receptacle lid is shown. For convenience, all elements which correspond to those shown in FIG. 7-9 will be numbered identically. A feed tube penetrating element 140 is disposed at the lower end of the feed tube 106. As shown in detail in FIG. 11, the penetrating element 140 includes a pair of crossing internal walls 142 which terminate in a pointed blade structure 144. The blade structure 144 leaves four separate flow passages 146 arranged in quadrants within the feed tube 104.

A plurality of similar penetrating structures 150 are provided for both piercing the receptacle lid and simultaneously providing fluidization air inlet paths. The penetrating structures 150 may be provided in a carrier plate 152 or similar supporting structure. The penetrating structures 150 will have a similar conical blade structure to that described previously for the feed tube penetrating structure 140. Thus, the structure of FIG. 10 can provide for both the feed tube penetration and the peripherally arranged fluidization air penetrations in the penetrable lid of a medicament receptacle in a single motion where the lid is drawn against the gasket 112 of the feed tube assembly 100.

FIG. 11B illustrates an alternative penetrating structure 151 formed by machining the end of a tube along two converging planes. The resulting pointed elements are then pressed together to form the structure having openings 153. The penetrating element 151 is advantageous since it peels back the lid as it is penetrated, leaving the openings 153 clear to receive powder. The penetrating structure 151 could be fabricated from molded plastic as well as machined metal.

Figure 12A:
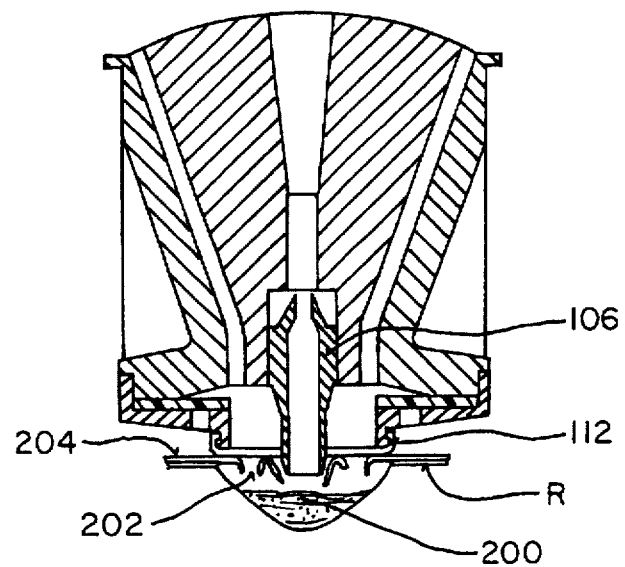
Figure 12B:
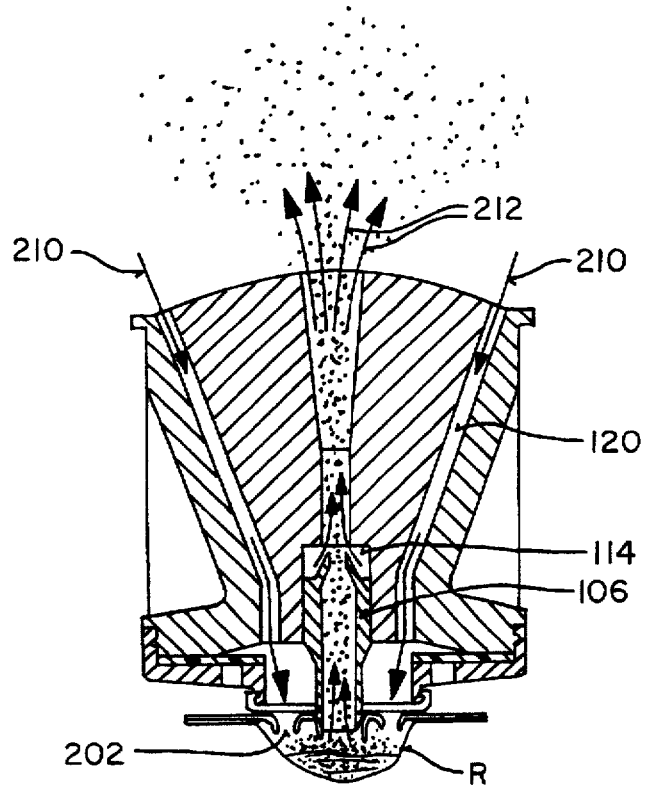
Figure 12C:
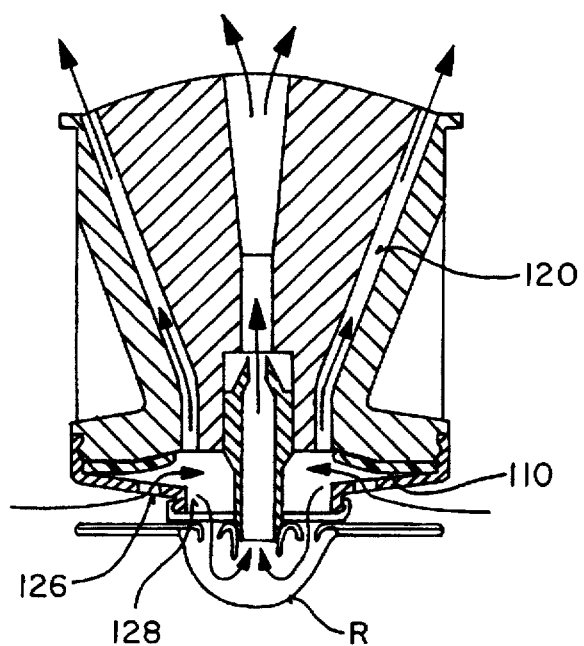

Referring now to FIGS. 12A–12C, use of the feed tube assembly 100 of FIGS. 7–9 will be described in more detail. Initially, a medicament receptacle R having preformed feed tube and fluidization air penetrations 200 and 202 is engaged against the gasket 112, as illustrated in FIG. 12A. Gasket 112 provides a seal against penetrable lid 204 of the receptacle R. The inlet end of feed tube 106 is shown to penetrate the lid 104, but it will be appreciated that such penetration is not essential since a seal will be provided by the gasket 112. Penetration may be desirable, however, since the lid flaps which surround the penetration 200 will be held open.

After the receptacle R is in place, a burst of high pressure air is introduced into the open cavity 114, as shown in FIG. 12B. The high pressure air flows past outlet end of the feed tube 106, inducing a flow of fluidization air through the receptacle R. In particular, fluidization air is drawn through the air flow channels 120 from the overlying plume chamber (not illustrated), as shown by arrows 210. The air drawn in through the air flow channels 120 enters the receptacle through penetrations 202, thus fluidizing the powder and drawing the powder out through the feed tube 106. The air flow through the feed tube thus entrains the powder and combines the powder with high pressure gas flow at the outlet end of the feed tube. The combined powder, fluidization air, and high pressure dispersion gas is then introduced into the plume chamber, as shown by arrows 212.

After the powder has been dispersed, patient will inhale from the plume chamber which will cause a reverse flow of air through the air flow channels 120, as illustrated in FIG. 12C, ambient air will enter the central opening 128 through apertures 126 as the flexible valve element 110 opens. The air which enters through apertures 126 will primarily pass through the air flow channels 120. A portion, however, may pass back into the receptacle R and upward through the feed tube into the plume chamber. Such flow through the receptacle will further empty the receptacle of any powder which may remain.

Although the foregoing invention has been described in some detail by way of illustration and example, for purposes of clarity of understanding, it will be obvious that certain changes and modifications may be practiced within the scope of the appended claims.

What is claimed is:

1. A method for aerosolizing a powder contained in a receptacle having an access surface, said method comprising coupling a powder inlet end of a feed tube having a central axis with a penetration in the access surface; and flowing a high pressure gas stream past a portion of the feed tube that is spaced apart from the inlet and the gas stream converging with the portion at an acute angle as measured between the gas stream and the central axis at the inlet end, so that a predetermined amount of powder in the receptacle is fluidized, drawn axially through the tube, and dispersed in the high velocity gas stream to form an aerosol.

2. A method as in claim 1, further comprising forming the penetration in the access surface prior to inserting the feed tube.

3. A method as in claim 1, wherein the penetration in the access surface is formed as the powder inlet end is inserted.

4. A method as in claim 1, further comprising forming at least two spaced-apart penetrations in the access surface, wherein the other penetration permits fluidization air to sweep the receptacle as the powder is drawn through the feed tube.

5. A method as in claim 1, further comprising advancing a plurality of powder-containing receptacles past the feed tube, whereby powder may be drawn sequentially and dispersed from each receptacle.

6. A method as in claim 1, wherein a fixed volume of high pressure gas in the range from 2 ml to 25 ml (STP) is flowed past the outlet end, resulting in a discrete volume of aerosolized powder, further comprising capturing substantially the entire volume of aerosolized powder in a plume capture chamber, wherein the powder is available for subsequent inhalation by a patient.

7. A method as in claim 6, wherein at least a portion of gas in the chamber is directed back to the receptacle to provide fluidization gas as the powder is withdrawn through the feed tube.

8. A method as in claim 1, wherein the high pressure air stream is flowed past the feed tube at an angle in the range from 12.5° to 65° relative to the axial direction.

9. A method as in claim 1, wherein the predetermined amount is at least 70% by weight of the amount of powdered medicament initially present in the receptacle.

10. Apparatus for aerosolizing a powder contained in a receptacle having a puncturable access surface, said apparatus comprising:

a base enclosure;

a holder within the base enclosure for supporting the receptacle at a fluidization location;

a feed tube within the base enclosure having an inlet end at a fluidization location; and means for flowing a high pressure gas stream past a portion of the feed tube which is spaced apart from the inlet end, wherein the gas stream converges with the feed tube at an acute angle as measured between the gas stream and the inlet end, wherein powder is fluidized from a receptacle in the holder and extracted axially through the tube and dispersed in the high pressure air stream to form an aerosol.

11. Apparatus as in claim 10, wherein the receptacle holder comprises means for advancing a continuous web which carries a plurality of receptacles thereon, whereby individual receptacles can be sequentially moved to the fluidization location.

12. Apparatus as in claim 11, wherein the means for advancing comprises a cartridge which is removably mounted in the base enclosure, said continuous web being movably mounted in said cartridge.

13. Apparatus as in claim 12, wherein the feed tube is fixedly mounted within the base enclosure and wherein the means for advancing comprises means for reciprocating the cartridge relative to the feed tube.

14. Apparatus as in claim 13, further comprising means for piercing a hole in the access surface prior to inserting the inlet end of the feed tube.

15. Apparatus as in claim 14, wherein the piercing means forms at least two spaced-apart holes in the access surface, wherein one hole couples to the feed tube and the other permits the entry of fluidization air to sweep the receptacle as powder is extracted through the feed tube.

16. Apparatus as in claim 15, further comprising a plume capture chamber in the base enclosure and means for directing air from an interior of the plume capture chamber to the receptacle, whereby said directed air will enter the receptacle to provide fluidization air as powder is drawn therefrom.

17. Apparatus as in claim 13, further comprising means for piercing a hole in the access surface simultaneously with inserting the inlet end of the feed tube.

18. Apparatus as in claim 15, wherein the piercing means comprises a fixed piercing mechanism which is disposed to piercing mechanism holes in the access surface of a receptacle as the cartridge is reciprocated relative to the feed tube.

19. Apparatus as in claim 10, further comprising a plume capture chamber disposed on the base to capture powder dispersed in said high velocity air stream, said chamber having a mouth piece at an end remote from the base.

20. Apparatus as in claim 10, wherein the means for flowing comprises a pump or other pressurized gas source in the base enclosure for abruptly releasing a pressurized volume of air to form the high velocity air stream.

21. Apparatus for aerosolizing a powder, said apparatus comprising:
 a feed tube having an inlet end, an outlet end, and a lumen defining an axial flow path therebetween;
 means for flowing at least one high pressure gas stream past said outlet end in a direction which converges with the axial flow path at an angle in the range from 12.5° to 65° and
 a diffuser tube extending from the outlet end of the feed tube and having a lumen coaxially aligned with the feed tube lumen, wherein the diameter of the diffuser tube lumen increases in a direction away from the outlet end of the feed tube.

22. Apparatus as in claim 21, wherein the flowing means includes at least one gas conduit which converge with the flow path.

23. Apparatus as in claim 21, wherein the flowing means provides a total lumen area ($A_1$) in the range from 0.05 mm$^2$ to 0.3 mm$^2$ and the feed tube has a lumen area ($A_2$) in the range from 0.5 mm$^2$ to 10 mm$^2$.

24. Apparatus as in claim 21, wherein the diffuser tube lumen diverges at a half angle of 2° to 10° over a length in the range from 0.5 cm to 5 cm.

25. Apparatus as in claim 21, further comprising a mixing volume disposed between the outlet end of the feed tube and the diffuser tube, said mixing volume having a constant diameter along its length.

26. Apparatus as in claim 25, wherein the mixing volume has a length which is from one to five times its diameter.

27. An improved method for aerosolizing a powdered medicament, said method being of the type wherein the powder is entrained and suspended in a flowing gas stream, wherein the improvement comprises inserting an inlet end of the feed tube into a receptacle containing the powdered medicament and flowing a high pressure gas stream past an outlet end of the feed tube which is downstream from the inlet end to induce air flow from the receptacle, through the tube, and into the flowing gas stream, wherein the powdered medicament is entrained in the air flow through the tube and combined with the high pressure gas stream, wherein the powdered medicament passes through a diffuser tube which diverges in a direction away from the outlet end of the feed tube and wherein the gas stream is flowed past the outlet end at an acute angle as measured between the gas stream and the inlet end.

28. A method for aerosolizing a powder contained in a receptacle having an access surface, said method comprising:
 coupling a powder inlet end of a feed tube having a central axis with a penetration in the access surface; and
 flowing a high pressure gas stream past a portion of the feed tube that is spaced apart from the powder inlet, the gas stream converging with the portion at an acute angle as measured between the gas stream and the central axis at the inlet end, the angle being selected to provide a sufficient gas flow through the feed tube so that a predetermined amount of powder in the receptacle is fluidized, drawn axially through the tube, and dispersed in the high velocity gas stream to form an aerosol, the angle further being selected to create shear forces within the feed tube sufficient to beak down agglomerates within the powder.

29. A method as in claim 28, further comprising forming the penetration in the access surface prior to inserting the feed tube.

30. A method as in claim 28, wherein the penetration in the access surface is formed as the powder inlet end is inserted.

31. A method as in claim 28, further comprising forming at least two spaced-apart penetrations in the access surface, wherein the other penetration permits fluidization air to sweep the receptacle as the powder is drawn through the feed tube.

32. A method as in claim 28, further comprising advancing a plurality of powder-containing receptacles past the feed tube, whereby powder may be drawn sequentially and dispersed from each receptacle.

33. A method as in claim 28, wherein a fixed volume of high pressure gas in the range from 2 ml to 25 ml (STP) is flowed past the outlet end, resulting in a discrete volume of aerosolized powder, further comprising capturing substantially the entire volume of aerosolized powder in a plume capture chamber, wherein the powder is available for subsequent inhalation by a patient.

34. A method as in claim 33, wherein at least a portion of gas in the chamber is directed back to the receptacle to provide fluidization gas as the powder is withdrawn through the feed tube.

35. A method as in claim 28, wherein the high pressure air stream is flowed past the feed tube at an angle in the range from 12.5° to 65° relative to the axial direction.

36. A method as in claim 28, wherein the predetermined amount is at least 70% by weight of the amount of powdered medicament initially present in the receptacle.

37. A method for aerosolizing a powder contained in a receptacle, said method comprising:

coupling a powder inlet end of a feed tube with a penetration in the receptacle; and abruptly releasing a gas from a pressurized source and directing the released gas in a high pressure gas stream past a portion of the feed tube which is spaced apart from the powder inlet, wherein the high velocity air stream is flowed cast the outlet end of the feed tube at an angle in the range from 12.5° to 65° as measured between the gas stream and the inlet end;

wherein the high pressure gas stream fluidizes powder in the receptacle and draws the fluidized powder through the reed tube and into the high pressure gas stream to form the aerosol, and wherein the high pressure gas stream produces a flow at the portion of the feed tube sufficient to provide shear forces to break down agglomerates within the powder.

38. A method as in claim 37, further comprising forming the penetration in the access surface prior to inserting the feed tube.

39. A method as in claim 37, wherein the penetration is the access surface is formed as the powder inlet end is inserted.

40. A method as in claim 37, further comprising forming at least two spaced-apart penetrations in the access surface, wherein the inlet end is coupled with one penetration and the other penetration permits fluidization air to sweep the receptacle as the powder is drawn through the feed tube.

41. A method as in claim 37, further comprising advancing a plurality of powder-containing receptacles past the feed tube, whereby powder may be drawn sequentially and dispersed from each receptacle.

42. A method as in claim 37, further comprising capturing substantially the entire volume of aerosolized powder in a plume capture chamber, wherein the powder is available for subsequent inhalation by a patient.

43. A method as in claim 42, wherein at least a portion of gas in the chamber is directed back to the receptacle to provide fluidization gas as the powder is withdrawn through the feed tube.

44. A method as in claim 37, wherein at least 70% by weight of the powder initially present in the receptacle is fluidized and drawn into the high pressure gas stream.

45. Apparatus for aerosolizing a powder, said apparatus comprising:

a feed tube having an inlet end, an outlet end, and a lumen defining an axial flow path therebetween; and at least one gas conduit spaced apart from the inlet end of the feed tube for flowing at least one high pressure gas stream past said outlet end in a direction which converges with the axial flow path at an acute angle relative to the inlet end; and a diffuser tube extending from the outlet end of the feed tube and having a lumen coaxially aligned with the feed tube lumen, wherein the cross sectional area of the diffuser tube lumen increases in a direction away from the outlet end of the feed tube.

46. Apparatus as in claim 45, wherein the acute angle is in the range from about 12.5° to 65°.

47. Apparatus as in claim 45, wherein the gas conduit provides a total lumen area ($A_1$) in the range from 0.05 mm$^2$ to 0.3 mm$^2$ and the feed tube has a lumen area ($A_2$) in the range from 0.5 mm$^2$ to 10 mm$^2$.

48. Apparatus as in claim 45, wherein the diffuser tube lumen diverges at a half angle of 2° to 10° over a length in the range from 0.5 cm to 5 cm.

49. Apparatus as in claim 45, further comprising a mixing volume disposed between the outlet end of the feed tube and the diffuser tube, said mixing volume having a constant diameter along its length.

50. Apparatus as in claim 49, wherein the mixing volume has a length which is from one to five times its diameter.

* * * * *